United States Patent
Yahiaoui et al.

(10) Patent No.: US 6,767,508 B1
(45) Date of Patent: Jul. 27, 2004

(54) NONWOVENS MODIFIED WITH ALKYL POLYGLYCOSIDE SURFACTANTS

(75) Inventors: Ali Yahiaoui, Roswell, GA (US); Matthew David Young, Kennesaw, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 476 days.

(21) Appl. No.: 09/724,318

(22) Filed: Nov. 28, 2000

(51) Int. Cl.$^7$ .............. A61L 2/16; B32B 27/00; A61F 13/15
(52) U.S. Cl. .............. 422/28; 442/123; 442/164; 604/360
(58) Field of Search .............. 422/28; 442/123, 442/164; 604/360

(56) References Cited

U.S. PATENT DOCUMENTS

| | | |
|---|---|---|
| 3,338,992 A | 8/1967 | Kinney |
| 3,341,394 A | 9/1967 | Kinney |
| 3,485,706 A | 12/1969 | Evans |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,901,236 A | 8/1975 | Assarsson et al. |
| 4,076,633 A | 2/1978 | Edwards et al. |
| 4,100,324 A | 7/1978 | Anderson et al. |
| 4,286,082 A | 8/1981 | Tsubakimoto et al. |
| 4,340,563 A | 7/1982 | Appel et al. |
| 4,725,489 A | 2/1988 | Jones et al. |
| 4,753,844 A | 6/1988 | Jones et al. |
| 4,818,464 A | 4/1989 | Lau |
| 4,938,888 A | 7/1990 | Kiefer et al. |
| 5,342,534 A | 8/1994 | Skrobala et al. |
| 5,542,950 A | 8/1996 | Cole et al. |
| 5,573,707 A | 11/1996 | Cole et al. |
| 5,612,045 A | 3/1997 | Syverson |
| 5,719,113 A | 2/1998 | Fendler et al. |
| 5,833,719 A | 11/1998 | Francois et al. |
| 5,856,290 A | 1/1999 | van Buskirk et al. |
| 5,863,887 A | 1/1999 | Gillette |
| 5,888,949 A | 3/1999 | Cole et al. |
| 5,931,823 A | 8/1999 | Stokes et al. |
| 5,932,495 A | 8/1999 | Boney et al. |
| 5,951,991 A | 9/1999 | Wagner et al. |
| 6,017,832 A | 1/2000 | Yahiaoui et al. |
| 6,599,521 B1 * | 7/2003 | Resheski-Wedepohl et al. . 424/430 |
| 6,676,957 B1 * | 1/2004 | Resheski-Wedepohl et al. . 424/430 |

FOREIGN PATENT DOCUMENTS

| | | |
|---|---|---|
| WO | 95/09605 | 4/1995 |
| WO | 98/09662 | 3/1998 |
| WO | 99/61079 | 12/1999 |

* cited by examiner

Primary Examiner—E. Leigh McKane
(74) Attorney, Agent, or Firm—Pauley Petersen & Erickson

(57) ABSTRACT

A nonwoven fabric treated with an alkyl polyglycoside surfactant solution results in a heterogeneous system having antibacterial activity when in contact with an aqueous source of bacteria. The antibacterial activity imparted to the nonwoven fabric renders the nonwoven fabric useful in a wide variety of absorbent products, such as personal care products and medical absorbent products, which are typically exposed to aqueous sources of bacteria. Furthermore, the alkyl plyglycoside surfactant is virtually non-irritating and non-sensitizing to human skin.

23 Claims, No Drawings

NONWOVENS MODIFIED WITH ALKYL POLYGLYCOSIDE SURFACTANTS

FIELD OF THE INVENTION

This invention relates to a nonwoven web having antimicrobial and bactericidal properties. More particularly, the invention is a heterogeneous system including a nonwoven web treated with an alkyl polyglycoside surfactant in contact with an aqueous source of bacteria.

BACKGROUND OF THE INVENTION

Nonwoven fabrics can be used to produce a wide variety of materials suitable for a broad range of applications. For example, nonwovens of light basis weight and open structure are used in personal care items such as disposable diapers. More particularly, such nonwovens can be used as liner fabrics that provide dry skin contact but readily transmit fluids to more absorbent materials which may also be nonwovens of a different composition and/or structure. Nonwovens of heavier weights may be designed with pore structures making them suitable for filtration, absorbent and barrier applications such as wipers or protective garments for medical, veterinary or industrial uses. Even heavier weight nonwovens have been developed for recreational, agricultural and construction uses. These are but a few of the practically limitless examples of types of nonwovens and their uses that will be known to those skilled in the art who will also recognize that new nonwovens and uses are constantly being identified. The present invention has general applicability to nonwovens as will be apparent to one skilled in the art, and it is not to be limited by reference or examples relating to specific nonwovens which are merely illustrative.

There have also been developed different treatments for enhancing specific properties of nonwovens. For example, properties such as wettability by one or more fluids, repellency to one or more fluids, electrostatic characteristics, conductivity, and softness, can be altered or improved through treatment with specific compositions. Still, further enhanced properties of nonwovens are desirable.

In particular, personal care items produced from nonwoven webs typically come in contact with bacteria as part of their intended use. There is thus a need or desire for a nonwoven fabric having effective antibacterial properties.

SUMMARY OF THE INVENTION

The present invention is directed to a heterogeneous antibacterial system, and a method of reducing bacterial growth in a nonwoven web. The heterogeneous antibacterial system includes a nonwoven web treated with an alkyl polyglycoside surfactant. Used to combat an aqueous source of bacteria, the alkyl polyglycoside surface treatment imparts antimicrobial and bactericidal properties to the nonwoven substrate.

The alkyl polyglycoside surfactant solution can be applied to the nonwoven web in dilute concentrations, generally 0.3–20%, by various saturation, spray, printing, and foam methods. The intrinsic antimicrobial and bacteriostatic properties of the surfactant solution are transferred to the nonwoven web, yet the surfactant solution is virtually non-irritating and non-sensitizing to human skin.

The surfactant treated nonwoven with antimicrobial and bactericidal properties can be used in a broad range of hygienic applications. For example, a nonwoven web treated with an alkyl polyglycoside-based formulation can be beneficial as an antibacterial wipe, as a bandage or wound dressing, or as a treatment for personal care materials to promote skin health, such as prevention of diaper rash, or other types of skin irritation. Furthermore, the treated nonwoven web can be placed in a personal care product in a number of strategic locations designed to prevent bacterial activity. The treated nonwoven can be a liner for direct skin contact for skin health benefits or in layers below the liner, such as surge layers, distribution layers, or retention layers, to control the activity of bacteria that causes malodor formation from retained body fluids. The nonwoven web can be made of synthetic and/or natural fibers.

With the foregoing in mind, it is a feature and advantage of the invention to provide a method of reducing bacterial growth in a nonwoven web, resulting from exposure to an aqueous source of bacteria.

It is also a feature and advantage of the invention to provide a heterogeneous antibacterial system including a solid/liquid interface between a nonwoven web and an aqueous source of bacteria.

DEFINITIONS

Within the context of this specification, each term or phrase below will include the following meaning or meanings.

"Average fiber length" refers to a weighted average length of fibers determined using a Kajaani fiber analyzer Model No. FS-100 available from Kaja Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The average fiber lengths may be expressed by the following equation:

$$\sum_{X_i>0}^{k} (X_i * n_i)/n$$

where k=maximum fiber length, $X_i$=individual fiber length, $n_i$=number of fibers having length $X_i$ and n=total number of fibers measured.

"Hydrophilic" or "wettable" describes fibers or the surfaces of fibers which are wetted by the aqueous liquids in contact with the fibers. The fibers or the surfaces of the fibers may have been treated with a surfactant, a surfactant combination, or other finishing agents. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Layer" when used in the singular can have the dual meaning of a single element or a plurality of elements.

"Meltblown fiber" means fibers formed by extruding a molten thermoplastic material through a plurality of fine, usually circular, die capillaries as molten threads or filaments into converging high velocity heated gas. (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Nonwoven" and "nonwoven fabric or web" refer to material and webs of material which are formed without the aid of a textile weaving or knitting process. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof Furthermore, unless otherwise specifically limited, the term "polymer" shall include all possible geometrical configurations of the material. These configurations include, but are not limited to isotactic, syndiotactic and atactic symmetries.

"Pulp fibers" refer to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The starting material for the invention is a nonwoven web including a plurality of filaments made from one or more polymers treated with an alkyl polyglycoside surfactant solution. The nonwoven web may be a spunbond web, a meltblown web, a bonded carded web, or another type of nonwoven web, including natural and/or synthetic fibers, and may be present in a single layer or a multilayer composite including one or more nonwoven web layers. When the nonwoven web treated with the alkyl polyglycoside surfactant solution comes into contact with an aqueous source of bacteria, a resulting heterogeneous system exhibits antibacterial activity attributable to the alkyl polyglycoside component. Examples of aqueous bacteria against which this type of heterogeneous system is effective include *S. aureus, E. coli, E. cloacae*, and *C. albicans*.

The alkyl polyglycoside surfactant solution is applied externally to the surfaces of the nonwoven web filaments after they are formed. As an external surfactant, the alkyl polyglycoside solution may be applied by dipping, soaking, spraying, printing, foaming or otherwise coating the nonwoven web with a medium containing the surfactant. Such surfactant inclusion techniques are generally well known in the art.

The surfactant solution used in accordance with the invention includes a dilute concentration of alkyl polyglycoside in a range of about 0.3% to 20%, preferably about 0.3% to 15%, more preferably about 0.5% to 5%. The surfactant solution imparts antimicrobial and bactericidal properties to the nonwoven substrate and yet is virtually non-irritating and non-sensitizing to human skin.

If the surfactant is applied externally using a solvent, the solvent may be removed using conventional evaporation techniques. On a solvent-free weight basis, the surfactant solution should constitute about 0.3% to 20% by weight of the nonwoven fabric to which it is applied, preferably about 0.3% to 15% by weight, more preferably about 0.5% to 5% by weight. Higher levels of surfactant solution are less desirable, due to cost and other issues. Levels which are too low tend to impart less antibacterial activity to the nonwoven fabric.

A wide variety of thermoplastic polymers may be used to construct the nonwoven substrate, including without limitation polyamides, polyesters, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, polybutadiene, isobutylene-isoprene copolymers, and combinations of any of the foregoing. Polyolefins are preferred. Polyethylene and polypropylene homopolymers and copolymers are most preferred, including pulp/polypropylene. The webs may also be constructed of bicomponent or biconstituent filaments or fibers, as defined above. The nonwoven webs may have a wide variety of basis weights, preferably ranging from about 10 grams per square meter (gsm) to about 120 gsm.

The treated nonwoven fabric can be used in a wide variety of absorbent product applications including, in particular, personal care absorbent products. Personal care absorbent products include diapers, training pants, swim wear, absorbent underpants, baby wipes, adult incontinence products, and the like, as well as other surge and intake material products. The surfactant treated nonwoven fabric can be placed in a number of strategic locations in personal care products to prevent bacterial activity. For example, a primary use of the surfactant treated nonwoven fabric is that of a liner for direct skin contact, thereby providing skin health benefits, such as prevention of diaper rash or other types of skin irritation. When used as a liner or matrix for an absorbent media, the absorbent medium may include, for instance, pulp fibers alone or in combination with a superabsorbent material. Alternatively, the treated nonwoven can be a layer or layers of an absorbent medium below the liner or matrix to control the activity of bacteria that cause malodor formation from retained body fluids. The treated nonwoven fabric can also be used in medical absorbent products, including without limitation underpads, absorbent drapes, bandages, and medical wipes. The treated nonwoven fabric may also be used in protective garments, including medical garments, aprons and gowns, and industrial workwear.

The pulp fibers of the absorbent medium (in absorbent products) may be any high-average fiber length pulp, low-average fiber length pulp, or mixtures of the same. Preferred pulp fibers include cellulose fibers. The term "high average fiber length pulp" refers to pulp that contains a relatively small amount of short fibers and non-fiber particles. High fiber length pulps typically have an average fiber length greater than about 1.5 mm, preferably about 1.5–6 mm, as determined by an optical fiber analyzer, such as the Kajaani tester referenced in the Definitions under "average fiber length". Sources generally include non-secondary (virgin) fibers as well as secondary fiber pulp which has been screened. Examples of high average fiber length pulps include bleached and unbleached virgin softwood fiber pulps.

The term "low average fiber length pulp" refers to pulp that contains a significant amount of short fibers and non-fiber particles. Low average fiber length pulps have an average fiber length less than about 1.5 mm, preferably about 0.7–1.2 mm, as determined by an optical fiber analyzer such as the Kajaani tester referenced above. Examples of low fiber length pulps include virgin hardwood pulp, as well as secondary fiber pulp from sources such as office waste, newsprint, and paperboard scrap.

Examples of high average fiber length wood pulps include those available from the U.S. Alliance Coosa Pines Corporation under the trade designations Longlac 19, Coosa River 56, and Coosa River 57. The low average fiber length pulps may include certain virgin hardwood pulp and secondary (i.e., recycled) fiber pulp from sources including newsprint, reclaimed paperboard, and office waste. Mixtures of high average fiber length and low average fiber length pulps may contain a predominance of low average fiber length pulps. For example, mixtures may contain more than about 50% by weight low-average fiber length pulp and less than about 50% by weight high-average fiber length pulp.

The term "superabsorbent" or "superabsorbent material" refers to a water swellable, water-insoluble organic or inorganic material capable, under the most favorable conditions, of absorbing at least about 15 times its weight and, more desirably, at least about 30 times its weight in an aqueous solution containing 0.9% by weight sodium chloride.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,633 issued Feb. 28, 1978 to Edwards et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Superabsorbents are generally available in particle sizes ranging from about 20 to about 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® 880, available from Stockhausen, located in Greensboro, N.C. An example of a fibrous superabsorbent is OASIS® 101, available from Technical Absorbents, located in Grimsby, United Kingdom.

As indicated above, the nonwoven fabric may be a liner or a matrix for an absorbent medium. When employed as a matrix, the nonwoven filaments may be combined with pulp fibers and (optionally) a superabsorbent material using processes well known in the art. For example, a coform process may be employed, in which at least one meltblown diehead is arranged near a chute through which other materials are added while the web is forming. Coform processes are described in U.S. Pat. No. 4,818,464 to Lau and U.S. Pat. No. 4,100,324 to Ariderson et al., the disclosures of which are incorporated by reference. The substantially continuous bicomponent filaments and pulp fibers may also be combined using hydraulic entangling or mechanical entangling. A hydraulic entangling process is described in U.S. Pat. No. 3,485,706 to Evans, the disclosure of which is incorporated by reference.

When the thermoplastic nonwoven filaments are used as a matrix for an absorbent nonwoven web composite, the composite should contain about 5–97% by weight pulp fibers, preferably about 35–95% by weight pulp fibers, more preferably about 50–95% by weight pulp fibers. When a superabsorbent material is present, it should constitute about 5–90% by weight of the composite, preferably about 10–60% by weight, more preferably about 20–50% by weight. In either case, the thermoplastic nonwoven filament matrix should constitute about 3–95% by weight of the composite, preferably about 5–65% by weight, more preferably about 5–50% by weight.

As taught by the invention, an alkyl polyglycoside surfactant solution provides antibacterial activity that typically reduces nearly 100% of bacteria present within a day, or may increase in effectiveness as exposure duration increases. One example of a commercially available form of alkyl polyglycoside is GLUCOPON® 220 UP, which is a solution of 60% octylpolyglycoside and 40% water. In the examples below, the antimicrobial effect of GLUCOPON® 220 UP was compared to the antimicrobial effects of AHCOVEL® Base N-62, available from Hodgson Chemical Co., which is a blend of ethoxylated hydrogenated castor oil and sorbitan monooleate, and TRITON®, available from Union Carbide, which is an alkylphenol ethoxylate surfactant.

EXAMPLES

Example 1

This example compares the efficacy of three different preservative systems, namely 15% TRITON® in water, 18.75% AHCOVEL® Base N-62 in water, and 2.14% GLUCOPON® 220 UP in water, in terms of antimicrobial effectiveness. In this example, a pre-determined amount of test media were inoculated with pure cultures of five separate strains of bacteria. At specific time intervals, post-inoculation, the test media were assayed and surviving populations of the challenge microorganisms were determined. Efficacy of the three preservative systems was determined by logarithmic reduction of the challenge microorganisms, as shown in Tables 1–3.

The test media used included Letheen broth (BBL or equivalent) for preparing dilutions of inoculated test samples, and more specifically, to neutralize antimicrobial agents. Also, Microbial Content Test agar (MCT) (Difco or equivalent) was included to neutralize residual antimicrobial activity when plating samples. Sterile saline was included at 0.9%. Trypticase Soy Agar (TSA) (BBL or equivalent) was also included for the initial cultivation of test organisms or other agar media promoting vigorous growth.

The procedure was carried out by inoculating the surface of TSA agar slants with freshly grown stock culture and incubating at 34–36° Celsius for 18–24 hours. Following incubation, the cells were harvested from the slants using a small volume (<1 ml) of 0.9% sterile saline, and using a sterile applicator stick or other instrument to gently rub the slants and loosen the organisms. The wash was diluted in sufficient saline to reduce the microbial concentration to 10 million cells per ml. Alternatively, the cultures could be grown in suitable broth medium (i.e., Nutrient broth or TSB) 18–24 hours at 34–36° Celsius. The cells were then harvested by centrifugation and washing (3 times in sterile saline) to give 10 million cells per ml. The number of viable microorganisms was determined at the time of inoculation.

A 20 ml sample of the test media was then aseptically placed into a sterile container for each of the five organisms tested. Following plating, each sample container was inoculated with one of the five organisms by aseptically adding 0.1 ml of standardized inoculum to 20 ml of test media. The contents of each container were then mixed thoroughly. The resultant inoculum concentrations were approximately $1 \times 10^3$ colony forming units per gram (CFU/gram). The samples were incubated for 28 days. The samples containing a solution of 15% TRITON® in water were incubated at 32° Celsius, whereas the samples containing solutions of 18.75% AHCOVEL® Base N-62 in water and 2.14% GLUCOPON® 220 UP in water were incubated at ambient temperature, 20–25° Celsius.

Once the samples were prepared, the plate count was determined immediately. This "0" hour count was used to provide the initial number of organisms per sample, which was the baseline for the purposes of estimating the reduction in the number of organisms over time. Assays to determine the viable bacterial populations in the inoculated test media were conducted at selected time intervals of 1, 7, 14 and 21 days.

Tables 1–3 show the logarithmic reduction of the inoculum, wherein the initial inoculum in each instance is $10^3$ CFU/gram. For example, on Day 0, the logarithmic reduction of P. aeruginosa was $1000 \times 10^{-0.33} = 468$ CFU/gram as an actual count. The shaded areas indicated growth increase of the bacteria being tested. As can be seen in Table 1, Sample 1 containing 15% TRITON® is susceptible to some growth, particularly that of B. cepacia. Similarly, as can be seen in Table 2, Sample 2 containing 18.75% AHCOVEL® Base N-62 is also susceptible to some growth, particularly that of P. aeruginosa. In contrast, as can be seen in Table 3, Sample 3 containing alkyl polyglycoside in the form of 2.14% GLUCOPON® 220 UP demonstrates broad antimicrobial activity through systematic reduction of all bacteria.

TABLE 1

15% TRITON ® in water

| Day | P. aeruginosa | E. coli | S. aureus | B. cereus | B. cepacia |
|---|---|---|---|---|---|
| 0 | −0.33 | −0.31 | −0.24 | −4.38 | +1.46 |
| 1 | −2.57 | −0.66 | −1.80 | −3.74 | +0.8 |
| 2 | −3.78 | −2.06 | −2.24 | −4.70 | +1.34 |
| 7 | −2.73 | −3.34 | −2.48 | −4.70 | +1.51 |
| 14 | −0.35 | −3.74 | −2.74 | −4.74 | +1.46 |
| 21 | +1.40 | −4.74 | −3.44 | −4.74 | ND |

TABLE 2

18.75% AHCOVEL ® Base N-62 in water

| Day | P. aeruginosa | E. coli | S. aureus | B. cereus | B. cepacia |
|---|---|---|---|---|---|
| 0 | −0.38 | −0.08 | −0.29 | −4.46 | −0.89 |
| 1 | +0.26 | −0.28 | −0.29 | −3.74 | −0.70 |
| 2 | +0.34 | −0.33 | −1.49 | −1.00 | −1.59 |
| 7 | −0.80 | −0.02 | −1.40 | −4.70 | +0.37 |
| 14 | −0.52 | −0.46 | −1.76 | −4.74 | −0.02 |
| 21 | ND | ND | −1.79 | −4.74 | ND |

TABLE 3

2.14% GLUCOPON ® 220 UP in water

| Day | P. aeruginosa | E. coli | S. aureus | B. cereus | B. cepacia |
|---|---|---|---|---|---|
| 0 | −1.38 | −0.89 | −0.17 | −1.00 | −3.74 |
| 1 | −4.78 | −4.74 | −4.74 | −3.74 | −3.74 |

TABLE 3-continued 2.14% GLUCOPON ® 220 UP in water

| Day | P. aeruginosa | E. coli | S. aureus | B. cereus | B. cepacia |
|---|---|---|---|---|---|
| 2 | −4.78 | −4.74 | −4.74 | −0.00 | −4.74 |
| 7 | −4.70 | −4.70 | −4.70 | −4.70 | −4.70 |
| 14 | −4.78 | −4.74 | −4.74 | −4.74 | −4.74 |
| 21 | ND | ND | ND | ND | ND |

Example 2

This example quantitatively compares the degree of antibacterial activity caused by two different surfactants, namely 3% GLUCOPON® 220 UP and 3% AHCOVEL®, and a third sample of a 3:1 combination of these two surfactants, on swatches of a spunbond fabric made from polypropylene fibers which has a basis weight of about 0.4 osy. In this example, bactericidal activity is expected from the treated swatches of fabric inoculated with $2.40 \times 10^4$ to $1.70 \times 10^5$ CFU/set of five separate strains of bacteria, or combinations of strains of bacteria. After incubation, the bacteria were eluted from the swatches by shaking in known amounts of neutralizing solution. The number of bacteria present in the liquid was determined, and the percentage reduction by the treated specimen was calculated at specific time intervals, as shown in Tables 4–6.

The culture medium used in this example included a suitable broth/agar media, such as Nutrient, Trypticase Soy or Brain-Heart Infusion. Nutrient broth include 5 grams of peptone (Bacto-peptone), 3 grams of beef extract and up to 1000 ml of distilled water. The culture medium was heated to a boil to disperse the ingredients and was adjusted to pH 6.8±0.1 with 1N sodium hydroxide (NaOH) solution (this is not necessary if prepared, dehydrated medium is used). The culture medium was dispensed in 10 ml amounts in conventional bacteriological culture tubes, which were then plugged and sterilized at 103 kPA (15 psi) for 15 minutes. Next, 1.5% bacteriological agar was added to the Nutrient broth, and was then heated to boiling. The pH was then adjusted to 7.1±0.1 using NaOH solution, as necessary. The Nutrient agar was then dispensed in 15±1 ml amounts in conventional bacteriological culture tubes, plugged, and sterilized at 103 kPa (15 psi) for 15 minutes. Using a 4 mm inoculating loop, the culture was transferred daily in Nutrient broth. The cultures were incubated at 37°±2° Celsius.

The quantitative testing was carried out by cutting circular swatches 4.8±0.1 cm in diameter from the test fabric. The swatches were stacked in a 250 ml wide-mouth glass jar with a screw cap. The number of swatches used was that which would absorb 1.0±0.1 ml of inoculum, leaving no free liquid in the jar. Then, 1.0±0.1 ml of an appropriate dilution of a 24 hour broth culture of the test organism was applied so that the fabric swatches at "0" contact time (plated as soon as possible after inoculation) showed counts of roughly 1–2× $10^5$ organisms, as shown in Tables 4–6. The dilution of the test organism was made in Nutrient broth.

The swatches were placed in separate sterile petri dishes and inoculated with an even distribution of the inoculum. The swatches were then aseptically transferred to the jar and the jar tops were screwed on tightly to prevent evaporation. As soon as possible after inoculation ("0" contact time), 100±1 ml of neutralizing solution was added to each of the jars containing the inoculated treated test swatches. The neutralizing solution included ingredients to neutralize the specific antibacterial fabric treatment and to take care of any pH requirements of the fabrics. The jars were then shaken vigorously for one minute. Serial dilutions were made with water and plated on Nutrient agar. The jars were then incubated at 37°±2° Celsius for 18–24 hours. After incubating, 100±1 ml of neutralizing solution was added to the jars and the jars were shaken vigorously for one minute. Serial dilutions were made and plated on Nutrient agar.

Assays to determine the viable bacterial populations in the inoculated test material were conducted at selected time intervals of 1, 5 and 7 days. Until assayed, the samples were incubated at 37°±2° Celsius Table 4 shows the percent reduction of the bacteria attributable to a surfactant containing 3% GLUCOPON® 220 UP. Similarly, Table 5 shows the percent reduction of the bacteria attributable to a surfactant containing 3% AHCOVEL®. Table 6 shows the percent reduction of the bacteria attributable to a surfactant containing a 3:1 mixture of 3% AHCOVEL®/GLUCOPON® 220 UP. The shaded areas indicated growth increase of the bacteria being tested. As can be seen in Table 4, Sample 1 containing an alkyl polyglycoside is susceptible to some growth, particularly that of a combination of P. aeruginosa & B. cepacia. However, the alkyl polyglycoside appears to greatly reduce the growth of S. aureus, E. coli & E. cloacae, and C. albicans, with slight initial reduction of A. niger & T. luteus and greater reduction by the seventh day. In contrast, as can be seen in Table 5, Sample 2 containing AHCOVEL® alone greatly reduces growth in S. aureus, but not in any other samples. In fact, Sample 2 allows E. coli & E. cloacae and P. aeruginosa & B. cepacia to greatly increase in growth. Even Sample 3, which is a combination of alkyl polyglycoside and AHCOVEL®, does not prevent growth of bacteria, other than S. aureus, as well as alkyl polyglycoside alone.

TABLE 4

3% GLUCOPON ® 220 UP on 0.4 osy Spunbond

| | 0 Hour CFU/set | 1 Day % Reduction | 5 Day % Reduction | 7 Day % Reduction |
|---|---|---|---|---|
| S. aureus | $1.40 \times 10^5$ | −99.93 | −99.93 | −99.93 |
| E. coli & E. cloacae | $1.10 \times 10^5$ | −99.47 | −99.91 | −99.91 |
| P. aeruginosa & B. cepacia | $1.20 \times 10^5$ | +400 | +516 | +1400 |
| C. albicans | $1.70 \times 10^5$ | −84.71 | −91.76 | −99.94 |
| A. niger & T. luteus | $2.40 \times 10^4$ | −12.5 | −33.33 | −90 |

TABLE 5

3% AHCOVEL ® on 0.4 osy Spunbond

| | 0 Hour CFU/set | 1 Day % Reduction | 5 Day % Reduction | 7 Day % Reduction |
|---|---|---|---|---|
| S. aureus | $1.40 \times 10^5$ | −99.93 | −99.93 | −99.93 |
| E. coli & E. cloacae | $1.10 \times 10^5$ | +572 | +8990 | +9900 |
| P. aeruginosa & B. cepacia | $1.20 \times 10^5$ | +608 | +7400 | +11566 |
| C. albicans | $1.70 \times 10^5$ | −25.53 | −29.41 | +29.41 |
| A. niger & T. luteus | $2.40 \times 10^4$ | −4.17 | +16.67 | −54.17 |

TABLE 6

3% AHCOVEL ®/GLUCOPON ® 220 (3:1) on 0.4 osy Spunbond

| | 0 Hour CFU/set | 1 Day % Reduction | 5 Day % Reduction | 7 Day % Reduction |
|---|---|---|---|---|
| S. aureus | $1.40 \times 10^5$ | −99.93 | −99.93 | −99.93 |
| E. coli & E. cloacae | $1.10 \times 10^5$ | +1172 | +6990 | +5809 |
| P. aeruginosa & B. cepacia | $1.20 \times 10^5$ | +392 | +8233 | +9900 |
| C. albicans | $1.70 \times 10^5$ | −41.18 | +76.47 | +52.41 |
| A. niger & T. luteus | $2.40 \times 10^4$ | −12.5 | −20.83 | −99.96 |

While the embodiments disclosed herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A method of reducing bacterial growth in a nonwoven substrate, resulting from exposure to an aqueous source of bacteria, the method comprising the steps of:

treating the nonwoven substrate with an alkyl polyglycoside surfactant solution before exposing the substrate to the aqueous source of bacteria, wherein the nonwoven substrate comprises synthetic fibers and is treated by at least one of the group consisting of dipping, soaking, spraying, printing, and foaming the alkyl polyglycoside surfactant solution onto the nonwoven substrate.

2. The method of claim 1, wherein the alkyl polyglycoside surfactant solution comprises between 0.3% and 20% alkyl polyglycoside.

3. The method of claim 1, wherein the alkyl polyglycoside surfactant solution comprises between 0.3% and 15% alkyl polyglycoside.

4. The method of claim 1, wherein the alkyl polyglycoside surfactant solution comprises between 0.5% and 5% alkyl polyglycoside.

5. The method of claim 1, wherein the nonwoven substrate further comprises natural fibers.

6. The method of claim 1, wherein the nonwoven substrate comprises a liner material.

7. The method of claim 1, wherein the nonwoven substrate comprises a layer in a laminate material.

8. The method of claim 1, wherein the nonwoven substrate comprises a surge layer.

9. The method of claim 1, wherein the nonwoven substrate comprises a distribution layer.

10. The method of claim 1, wherein the nonwoven substrate comprises a retention layer.

11. The method of claim 1, wherein the nonwoven substrate comprises a layer in a diaper.

12. The method of claim 1, wherein the nonwoven substrate comprises a layer in a training pant.

13. The method of claim 1, wherein the nonwoven substrate comprises a layer in an absorbent underpant.

14. The method of claim 1, wherein the nonwoven substrate comprises a layer in a medical gown.

15. The method of claim 1, wherein the nonwoven substrate comprises a layer in a medical cap.

16. The method of claim 1, wherein the nonwoven substrate comprises a layer in a medical glove.

17. The method of claim 1, wherein the nonwoven substrate comprises a layer in a medical drape.

18. The method of claim 1, wherein the nonwoven substrate comprises a layer in a medical face mask.

19. The method of claim 1, wherein the nonwoven substrate comprises a layer in industrial workwear.

20. The method of claim 1, wherein the nonwoven substrate comprises a spunbonded web.

21. The method of claim 1, wherein the nonwoven substrate comprises a meltblown web.

22. The method of claim 1, wherein the nonwoven substrate comprises a bonded carded web.

23. The method of claim 1, wherein the nonwoven substrate comprises bicomponent polymer filaments including at least two distinct polymer components, wherein at least one of the polymer components is treated with the alkyl polyglycoside surfactant.

\* \* \* \* \*